United States Patent
Mao

(10) Patent No.: US 7,553,285 B2
(45) Date of Patent: Jun. 30, 2009

(54) DIAGNOSING PERIPHERAL VASCULAR DISEASE BY MONITORING OXYGEN SATURATION CHANGES DURING AN ACCUMULATION PHASE

(75) Inventor: Jimmy Jian-min Mao, Fremont, CA (US)

(73) Assignee: ViOptix Inc., Fremont, CA (US)

( * ) Notice: Subject to any disclaimer, the term of this patent is extended or adjusted under 35 U.S.C. 154(b) by 0 days.

(21) Appl. No.: 12/170,278

(22) Filed: Jul. 9, 2008

(65) Prior Publication Data

US 2008/0269620 A1 Oct. 30, 2008

Related U.S. Application Data

(63) Continuation of application No. 11/782,198, filed on Jul. 24, 2007, now abandoned, which is a continuation-in-part of application No. 10/838,142, filed on May 3, 2004, now Pat. No. 7,247,142.

(60) Provisional application No. 60/468,003, filed on May 5, 2003.

(51) Int. Cl.
*A61B 5/00* (2006.01)
*A61B 5/02* (2006.01)
(52) U.S. Cl. .................. 600/481; 600/500; 600/323
(58) Field of Classification Search ........... None
See application file for complete search history.

(56) References Cited

U.S. PATENT DOCUMENTS

| | | | |
|---|---|---|---|
| 6,863,656 B2 | 3/2005 | Lurie | |
| 6,909,912 B2 | 6/2005 | Melker | |
| 2003/0236452 A1 | 12/2003 | Melker et al. | |
| 2007/0016079 A1 | 1/2007 | Freeman et al. | |
| 2007/0024946 A1 | 2/2007 | Panasyuk et al. | |
| 2007/0038042 A1 | 2/2007 | Freeman et al. | |
| 2007/0249913 A1 | 10/2007 | Freeman et al. | |

OTHER PUBLICATIONS

Myers, DE et al., "Noninvasive Method for Measuring Local Hemoglobin Oxygen Saturation in Tissue Using Wide Gap Second Derivative Near-Infared Spectroscopy," Level1Diet, J Biomed Opt. May-Jun. 2005, accessed Mar. 25, 2008, <http://www.level1diet.com/893768_id>.

(Continued)

*Primary Examiner*—Robert L Nasser
(74) *Attorney, Agent, or Firm*—Aka Chan LLP

(57) ABSTRACT

Peripheral vascular disease is diagnosed through measurements of oxygen saturation. In a specific implementation, peripheral vascular disease is diagnosed based on changes in oxygen saturation in tissue. Ischemia is induced, and measurements of changes in oxygen saturation in tissue are made. Based on changes in oxygen saturation during an accumulation phase, a diagnosis is provided of whether a patient has or does not have peripheral vascular disease.

21 Claims, 12 Drawing Sheets

OTHER PUBLICATIONS

Kasel, Dustin, "Tissue Oxygen Saturation as a Non-Invasive Measurement for Cardiac Output," Nov. 18, 2007, accessed Mar. 25, 2008, –http://biomedprojects.org/home/projects/papers/tissue-oxygen-saturation-measurement-as-a-non-invasive-alternative-to-cardiac-output-1>.

Comerota, AJ et al., "Tissue (muscle) Oxygen saturation (StO2): A New Measure of Symptomatic Lower-Extremity Arterial Disease," Jobst Vascular Center, Oct. 2003, accessed Mar. 25, 2008, <http://www.ncbi.nlm.nih.gov/pubmed/14560221?dopt=Abstract>.

Kragelj, Rudi et al., "Parameters of Postocclusive Reactive Hyperemia Measured by Near Infrared Spectroscopy in Patients with Peripheral Vascular Disease and in Healthy Volunteers," Annals of Biomedical Engineering, vol. 29, pp. 311-320 (2001).

StO2 Recovery Rate

| PTS Result | PVD status | |
|---|---|---|
| | Positive | Negative |
| Positive | a = 10 (true positive) | b = 1 (false positive) |
| Negative | c = 0 (false negative) | d = 8 (true negative) |
| Sensitivity = a/(a+c) | 100% ± 0% ||
| Specificity = d/(b+d) | 89% ± 7% ||
| PPV = a/(a+b) | 91% ± 7% ||
| NPV = d/(c+d) | 100% ± 0% ||

*FIG. 7*

Recovery to 80%

| PTS Result | PVD status | |
|---|---|---|
| | Positive | Negative |
| Positive | a = 8 (true positive) | b = 0 (false positive) |
| Negative | c = 2 (false negative) | d = 9 (true negative) |
| Sensitivity = a/(a+c) | 80% ± 0% ||
| Specificity = d/(b+d) | 100% ± 7% ||
| PPV = a/(a+b) | 100% ± 7% ||
| NPV = d/(c+d) | 82% ± 0% ||

*FIG. 11*

DIAGNOSING PERIPHERAL VASCULAR DISEASE BY MONITORING OXYGEN SATURATION CHANGES DURING AN ACCUMULATION PHASE

CROSS-REFERENCE TO RELATED APPLICATIONS

This patent application is a continuation of U.S. patent application Ser. No. 11/782,198, filed Jul. 24, 2007 now abandoned, which is a continuation-in-part of U.S. patent application Ser. No. 10/838,142, filed May 3, 2004 and issued as U.S. Pat. No. 7,247,142 on Jul. 24, 2007, which claims priority to U.S. provisional patent application 60/468,003, filed May 5, 2003, which are incorporated by reference.

BACKGROUND OF THE INVENTION

The present invention relates to methods of diagnosing peripheral vascular disease (PVD) using measured changes in oxygen saturation in tissue. More specifically, the invention relates to diagnosing peripheral vascular disease from an analysis of oxygen saturation during recovery from ischemia (reduced or stoppage of blood flow).

Peripheral vascular disease is a condition that is exemplified by a narrowing of blood vessels to internal organs and muscles. Patients with peripheral vascular disease are four times more likely to have a myocardial infarction and three times more likely to have a stroke. The five year mortality rate for people with peripheral vascular disease is 30 percent. Peripheral vascular disease affects 20 percent of the elderly and 40 percent of diabetics.

It has been estimated that 8-12 million people in the United States are affected with this disease and the numbers are growing at a rate of five percent a year. Although these numbers show that peripheral vascular disease is a fairly common disease, peripheral vascular disease is often not diagnosed or is misdiagnosed. It has been estimated that 71 percent of physicians overlook a peripheral vascular disease condition in their patients.

It would be beneficial to have innovative techniques for diagnosing peripheral vascular disease. Additionally, it would be beneficial to have techniques of diagnosing peripheral vascular disease with relatively high accuracy rates.

BRIEF SUMMARY OF THE INVENTION

The present invention provides innovative techniques for diagnosing peripheral vascular disease. In a specific implementation, peripheral vascular disease is diagnosed based on changes in oxygen saturation in tissue. Ischemia is induced, and measurements of changes in oxygen saturation in tissue are made. Based on changes in oxygen saturation during an accumulation phase, a diagnosis is provided of whether a patient has or does not have peripheral vascular disease.

Techniques of the invention may be incorporated in devices or systems of the invention. For example, a device of the invention may use a technique or any combination or techniques described and then display a diagnosis of peripheral vascular disease (e.g., provide a visual indication on a screen of a positive or negative test result).

Generally, oxygen saturation in tissue of a patient is monitored as part of a postocclusive reactive hyperemic (PORH) test. For example, blood flow to a limb can be reduced or stopped by utilizing a pressure cuff. The oxygen saturation of the limb can be monitored before, during, or after ischemia. The changes in oxygen saturation observed during the monitoring are then used to diagnose whether the patient has peripheral vascular disease. In this manner, not only can peripheral vascular disease be readily diagnosed, the accuracy of the diagnoses can be relatively high.

In an embodiment, a method of diagnosing peripheral vascular disease includes: Oxygen saturation in tissue of a patient is measured during an accumulation phase. The oxygen saturation in the tissue during ischemia is then analyzed. The patient is diagnosed as having peripheral vascular disease according to changes in the oxygen saturation in the tissue during the accumulation phase. In some embodiments, the changes can be a rate of change of oxygen saturation or a time for oxygen saturation to reach a specific percentage, or both.

In an embodiment, a method of diagnosing peripheral vascular disease includes: Oxygen saturation in tissue of a patient is measured during an accumulation phase. A rate of change of oxygen saturation during ischemia is calculated. The patient is diagnosed as having peripheral vascular disease if the rate of change crosses a threshold. In some embodiments, the rate of change can be calculated at a midpoint of the accumulation phase.

In an embodiment, a method of diagnosing peripheral vascular disease includes: Oxygen saturation in tissue of a patient is measured during an accumulation phase. A time for oxygen saturation to reach a specified percentage during the accumulation phase is calculated. The patient is diagnosed as having peripheral vascular disease if the time for oxygen saturation to reach a specified percentage crosses a threshold.

In an embodiment, a method of diagnosing peripheral vascular disease includes: measuring oxygen saturation in tissue of a patient during an accumulation phase after ischemia; analyzing the oxygen saturation in the tissue during the accumulation phase; and diagnosing the patient as having peripheral vascular disease according to changes in the oxygen saturation in the tissue during the accumulation phase.

In an embodiment, an apparatus for diagnosing peripheral vascular disease includes: a device to cause ischemia in tissue; a probe that measures oxygen saturation in the tissue of a patient during an accumulation phase after induced ischemia; and a computer, connected to the probe, that analyzes the oxygen saturation in the tissue during the accumulation phase and diagnoses the patient as having peripheral vascular disease according to the oxygen saturation in the tissue during the accumulation phase.

In an embodiment, a method of diagnosing peripheral vascular disease includes: measuring oxygen saturation in tissue of a patient during an accumulation phase after ischemia; calculating a rate of change of oxygen saturation during the accumulation phase; and diagnosing the patient as having peripheral vascular disease if the rate of change crosses a threshold.

In an embodiment, an apparatus for diagnosing peripheral vascular disease includes: a probe that measures oxygen saturation in tissue of a patient during an accumulation phase after ischemia; and a computer, connected to the probe, that calculates a rate of change of oxygen saturation during the accumulation phase and diagnoses the patient as having peripheral vascular disease if the rate of change crosses a threshold.

In an embodiment, a method of diagnosing peripheral vascular disease includes: measuring oxygen saturation in tissue of a patient during an accumulation phase after ischemia; calculating a time for oxygen saturation to reach a specified percentage during the accumulation phase; and diagnosing the patient as having peripheral vascular disease if the time for oxygen saturation to reach a specified percentage crosses a threshold.

In an embodiment, an apparatus for diagnosing peripheral vascular disease includes: a probe that measures oxygen saturation in tissue of a patient during an accumulation phase after ischemia; and a computer, connected to the probe, that calculates a time for oxygen saturation to reach a specified percentage during the accumulation phase and diagnoses the patient as having peripheral vascular disease if the time for oxygen saturation to reach a specified percentage crosses a threshold.

In an embodiment, a method includes: measuring oxygen saturation of the tissue of the patient during an accumulation phase prior to ischemia; and diagnosing the patient as having peripheral vascular disease based on changes in the oxygen saturation of the tissue during an accumulation phase before ischemia.

In various embodiments, the method may include providing a visual indication of a positive diagnosis of peripheral vascular disease on a display when a measured rate of change in the oxygen saturation during an accumulation phase crosses a threshold value. The method may include providing a visual indication of a positive diagnosis of peripheral vascular disease on a display when a measured time for the oxygen saturation to cross a percentage value during the accumulation phase exceeds a specific time value.

The method may include providing a visual indication of a positive diagnosis of peripheral vascular disease on a display when a measured time, from a starting time value to an ending time value, for the oxygen saturation to cross a percentage value exceeds a specific time value, where the ending time is within the accumulation phase. The method may include providing a visual indication of a positive diagnosis of peripheral vascular disease on a display when a measured time, from a starting time value to an ending time value, for the oxygen saturation to cross a percentage value exceeds a specific time value, where the starting time is within the accumulation phase.

In an embodiment, a system for diagnosing peripheral vascular disease includes: a probe having a first detector input; a computer, connected to process signals received via the first detector input, to determine changes in oxygen saturation in tissue of a patient and make a diagnosis of peripheral vascular disease based on the oxygen saturation changes during an accumulation phase; and a display, connected to the computer, to provide a visual indication of a positive diagnosis of peripheral vascular disease.

In various specific embodiments, the diagnosis of peripheral vascular disease is positive when the computer determines a rate of change in the oxygen saturation crosses a threshold value during the accumulation phase before ischemia. The diagnosis of peripheral vascular disease is positive when a measured time for the oxygen saturation to cross a percentage value during the accumulation phase before ischemia exceeds a specific time value. The diagnosis of peripheral vascular disease is positive when a measured time, from a starting time value to an ending time value, for the oxygen saturation to cross a percentage value exceeds a specific time value, and the ending time is within the accumulation phase before ischemia. The diagnosis of peripheral vascular disease is positive when a measured time, from a starting time value to an ending time value, for the oxygen saturation to cross a percentage value exceeds a specific time value, and the starting time is within the accumulation phase before ischemia.

In various specific embodiments, the probe has a second detector input and a source output, and a first distance between the first detector input and the source output is different from a second distance between the second detector input and the source output. The probe has a second detector input, a first source output, and a second source output, and a first distance between the first detector input and the first source output is different from a second distance between the second detector input and the second source output. The probe has a second detector input, a first source output, and a second source output, and a first distance between the first detector input and the first source output is substantially the same as a second distance between the second detector input and the second source output.

Other features and advantages of the invention will become readily apparent upon review of the following description in association with the accompanying drawings, where the same or similar structures are designated with the same reference numerals.

BRIEF DESCRIPTION OF THE DRAWINGS

FIG. 7 shows results of diagnoses of patients for peripheral vascular disease utilizing the rate of recovery of oxygen saturation.

FIG. 11 shows results of diagnoses of patients for peripheral vascular disease utilizing the time oxygen saturation to recover a specified percentage.

DETAILED DESCRIPTION OF THE INVENTION

In the description that follows, the present invention will be described in reference to embodiments that diagnose peripheral vascular disease utilizing changes in oxygen saturation in tissue during recovery from ischemia. However, embodiments of the invention are not limited to any particular environment, application, or implementation. For example, although different techniques of monitoring changes in oxygen saturation will be described, the invention is not limited to the specific embodiments described below. Therefore, the description of the embodiments that follows is for purposes of illustration and not limitation.

Figure 1:
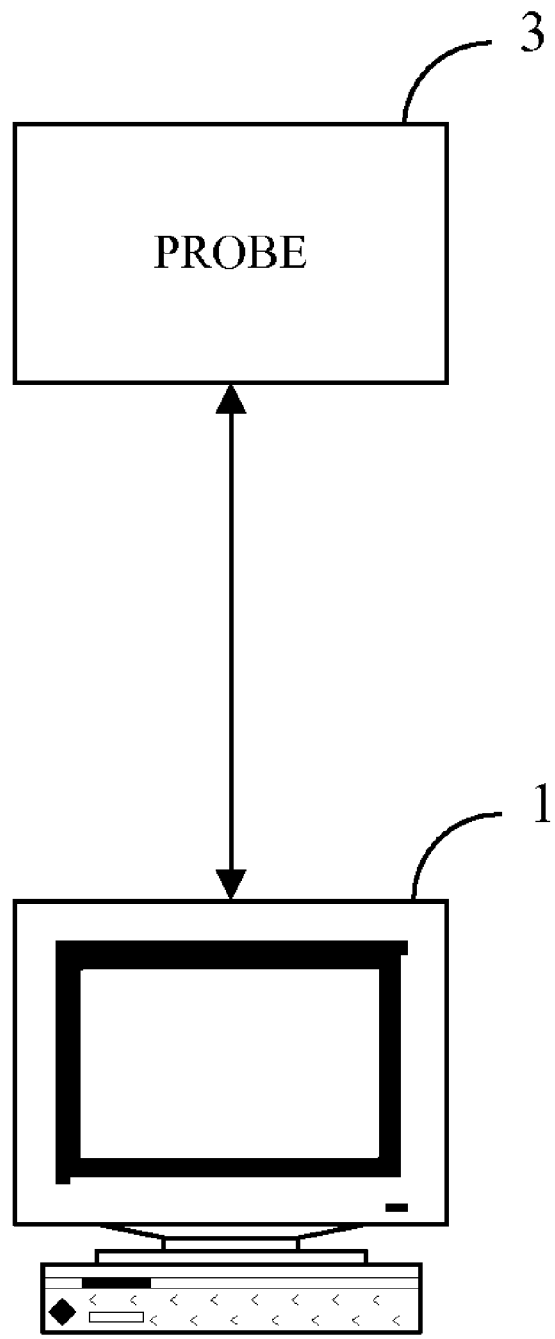
FIG. 1 shows an example of a computer system and probe for measuring oxygen saturation in tissue.

FIG. 1 shows an example of a system for diagnosing peripheral vascular disease. A computer system 1 is connected to a probe 3. Probe 3 is typically placed in close contact to a patient's tissue in order to collect data that can be analyzed by computer system 1 in order to determine oxygen saturation in the tissue.

In some embodiments, the system for measuring oxygen saturation in tissue is as described in U.S. patent application Ser. No. 09/877,515, filed Jun. 7, 2001, which issued as U.S. Pat. No. 6,587,703 on Jul. 1, 2003, which is incorporated by reference. For example, the oxygen saturation system can use continuous wave spectroscopy (CWS) to determine absolute values of concentrations of oxygenated and deoxygenated hemoglobins in a patient's tissue. In other embodiments, other systems for measuring oxygen saturation in tissue can be utilized.

Figure 2:
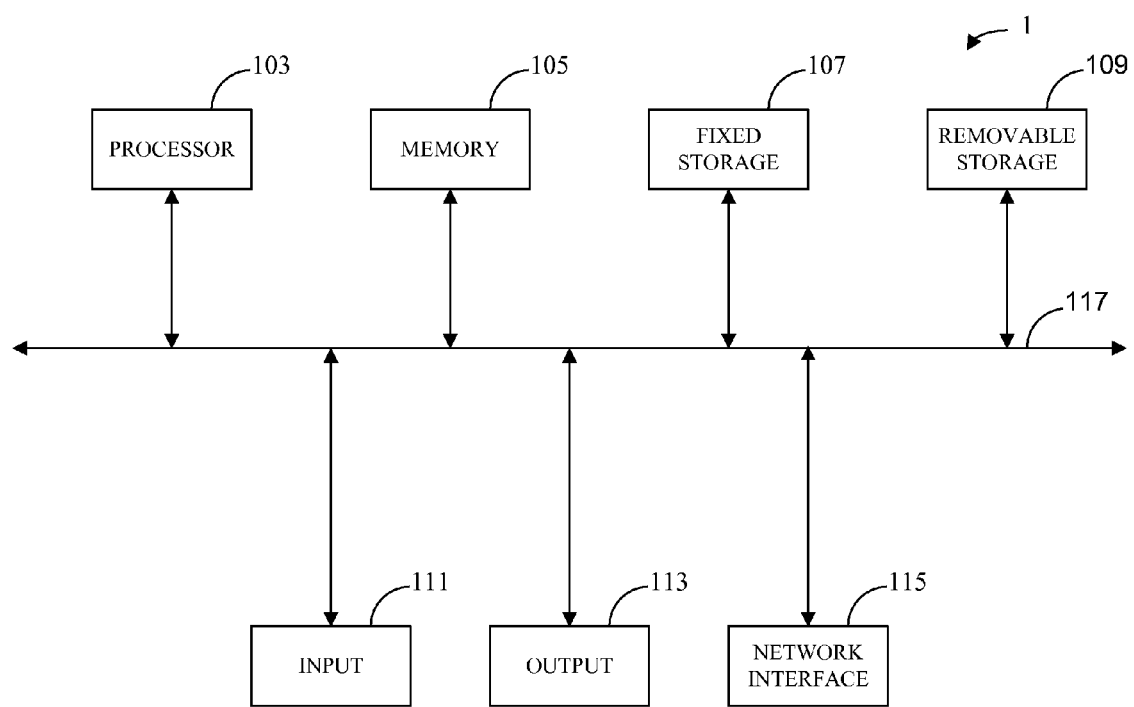
FIG. 2 illustrates a block diagram of a computer system that can be utilized in association with embodiments of the invention.

FIG. 2 shows a block diagram of components that can be present in computer systems that implement embodiments of the invention. A computer system 1 includes a processor 103 that executes instructions from computer programs (including operating systems). Although processors typically have memory caches also, processor 103 utilizes memory 105, which can store instructions or computer code and data.

A fixed storage (e.g., hard drives or drives) 107 can store computer programs and data such that it is typically persistent and provides more storage when compared to memory 105. A removable storage 109 provides mobility to computer programs and/or data that are stored thereon. Examples of removable storage are floppy disks, tape, CD-ROM, flash memory devices, and the like.

Memory 103, fixed storage 107, and removable storage 109 provide examples of computer readable storage media that can be utilized to store and retrieve computer programs incorporating computer codes that implement the invention, data for use with the invention, and the like. Additionally, a data signal embodied in a carrier wave (e.g., in a network including the Internet) can be the computer readable storage medium. An input 111 allows a user to interface with the system. Input can be done through the use of a keyboard, a mouse, buttons, dials, or any other input mechanism. An output 113 allows the system to provide output to the user. Output can be provided through a monitor, display screen, LEDs, printer, or any other output mechanism.

A network interface 115 allows the system to interface with a network to which it is connected. The system bus architecture of computer system 1 is represented by arrows 117. The components shown in FIG. 2 can be found in many computer systems. However, components can be added, deleted, and combined. Thus, FIG. 2 is for illustration purposes and not limitation.

Figure 3:
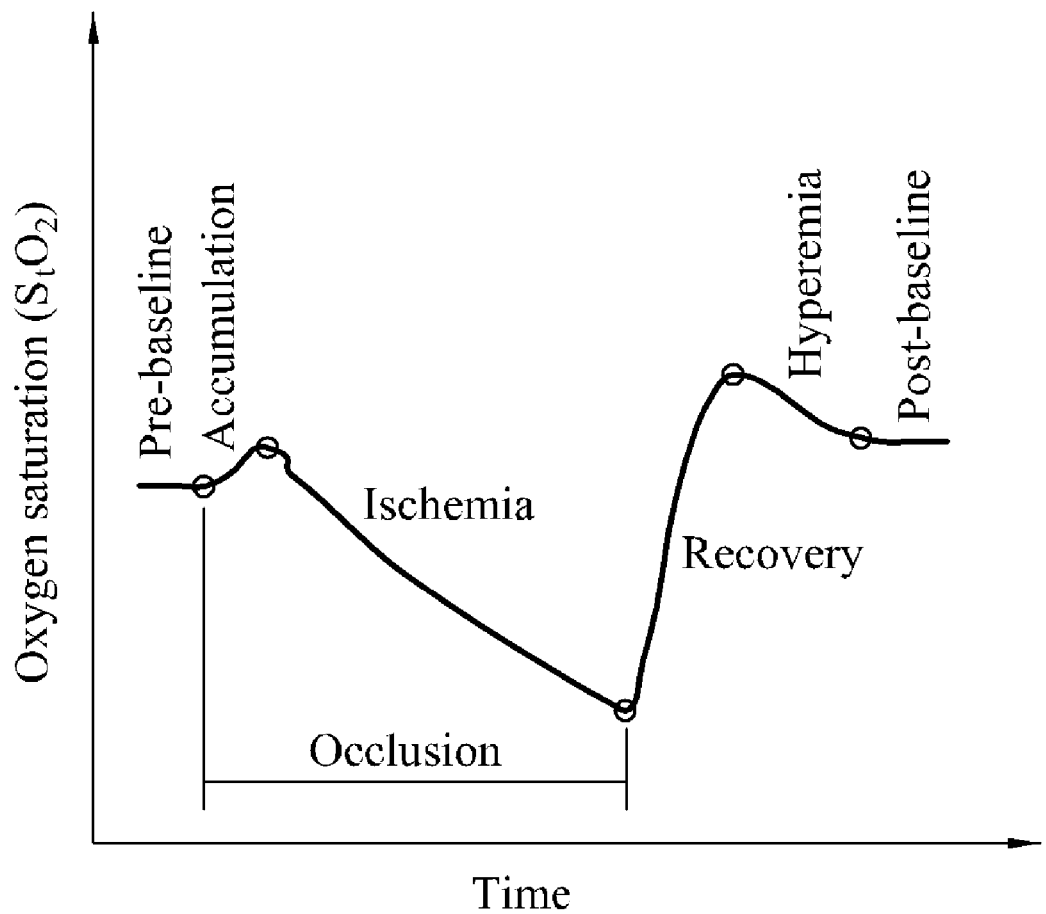
FIG. 3 shows a graph of oxygen saturation over time through induced ischemia and subsequent recovery.

FIG. 3 shows a graph of oxygen saturation through induced ischemia and subsequent recovery. The measurements were obtained as follows.

A subject was laying supine in a resting state. Sensors were positioned over the anterior tibialis muscle flat against the skin with minimal coupling pressure. Initial oxygen saturation measurements were then taken.

Occlusion of anterior blood flow to a lower limb was induced by inflating a cuff to 30 millimeter of mercury above systolic pressure. Cessation of blood flow was confirmed with a doppler. Occlusion was maintained for five minutes and then the occlusion was removed so that blood flow was rapidly restored. During this time, oxygen saturation was continuously monitored and recorded as indicated in the graph.

The graph in FIG. 3 can be broken into many different phases as shown. A prebaseline phase is where the cuff was not inflated and the subject was at rest. This stage shows the oxygen saturation level as a baseline before occlusion.

An accumulation phase is at the beginning of occlusion immediately following the cuff inflation, which causes oxy-hemoglobin accumulation in the tissue.

An ischemic phase is the period following the accumulation phase while the cuff remained inflated and oxygen was being consumed. As shown, oxygen saturation steadily declines during this phase.

A recovery phase is the beginning post occlusive period, immediately following the cuff deflation, while fresh arterial blood is returning and oxygen saturation increases rapidly. As shown, oxygen saturation rose higher than the pre baseline oxygen saturation (called "overshooting").

A hyperemia phase was the last phase of a post occlusive reactive hyperemic (PORH) test. In the hyperemia phase, oxygen saturation decreased from its peak due to overshooting and reached the post occlusive baseline phase.

Figure 4:
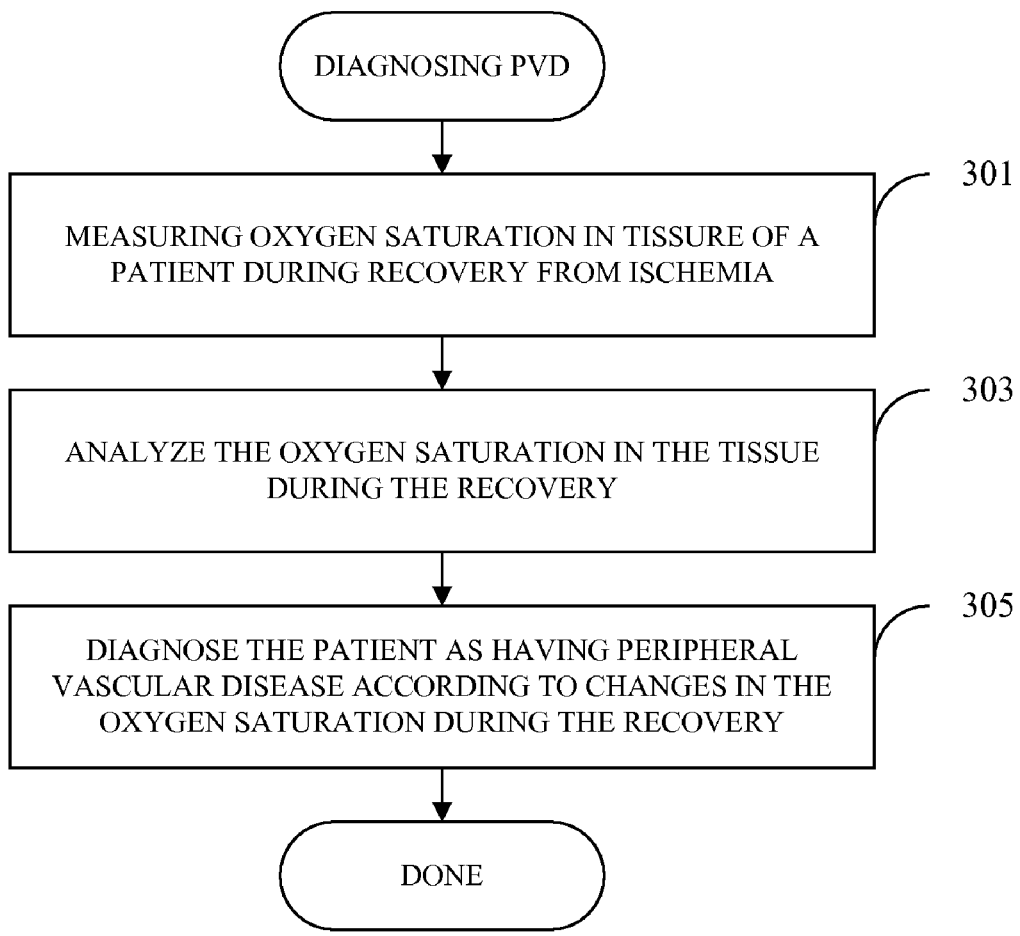
FIG. 4 shows a flow chart of a process of diagnosing peripheral vascular disease according to one embodiment of the invention.

Embodiments of the invention utilize changes in oxygen saturation during recovery from induced ischemia to diagnose peripheral vascular disease. FIG. 4 shows a flowchart of a process of diagnosing peripheral vascular disease utilizing changes in oxygen saturation during the recovery.

At a step 301, oxygen saturation in tissue of a patient during recovery from ischemia is measured. The oxygen saturation in the tissue during the recovery is analyzed at a step 303.

At a step 305, the patient is diagnosed as having peripheral vascular disease according to changes in the oxygen saturation during the recovery. The changes in oxygen saturation can be measured in various ways.

Figure 5:
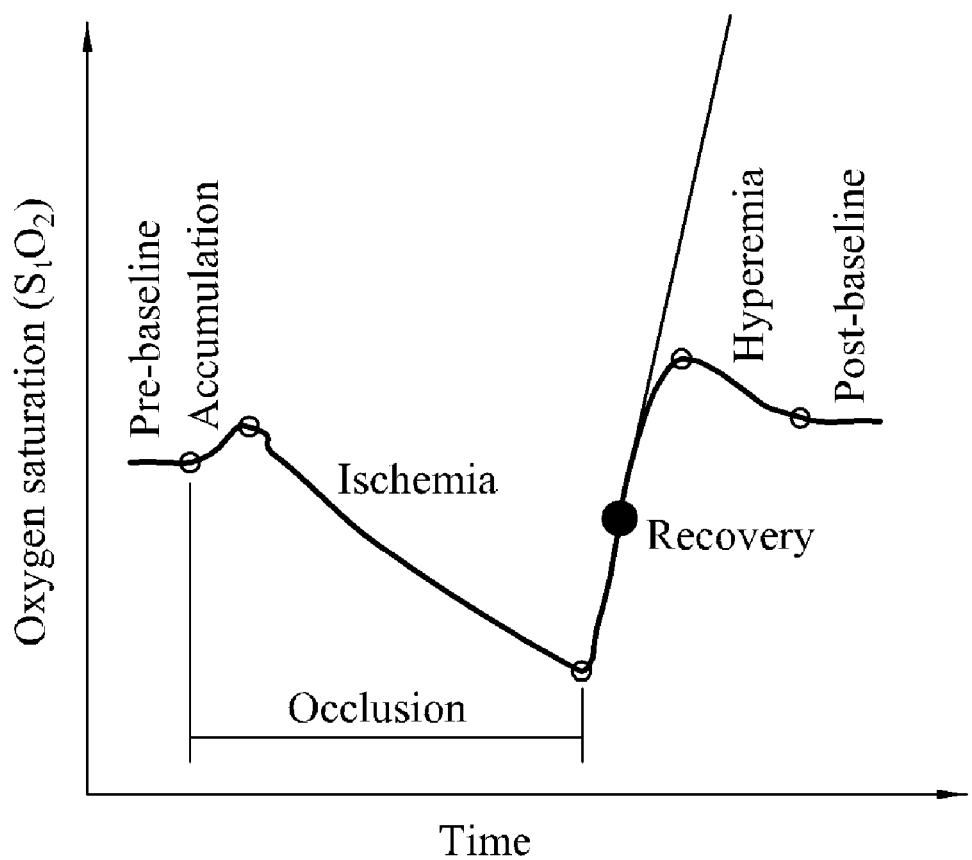
FIG. 5 shows a graph including the rate of change of oxygen saturation during recovery from ischemia.

In one embodiment, the changes in oxygen saturation are measured by the rate of change of oxygen saturation during recovery from ischemia. FIG. 5 shows a graph of the rate of recovery of oxygen saturation during recovery. As shown, the rate of change is measured at a midpoint in the recovery phase.

Figure 6:
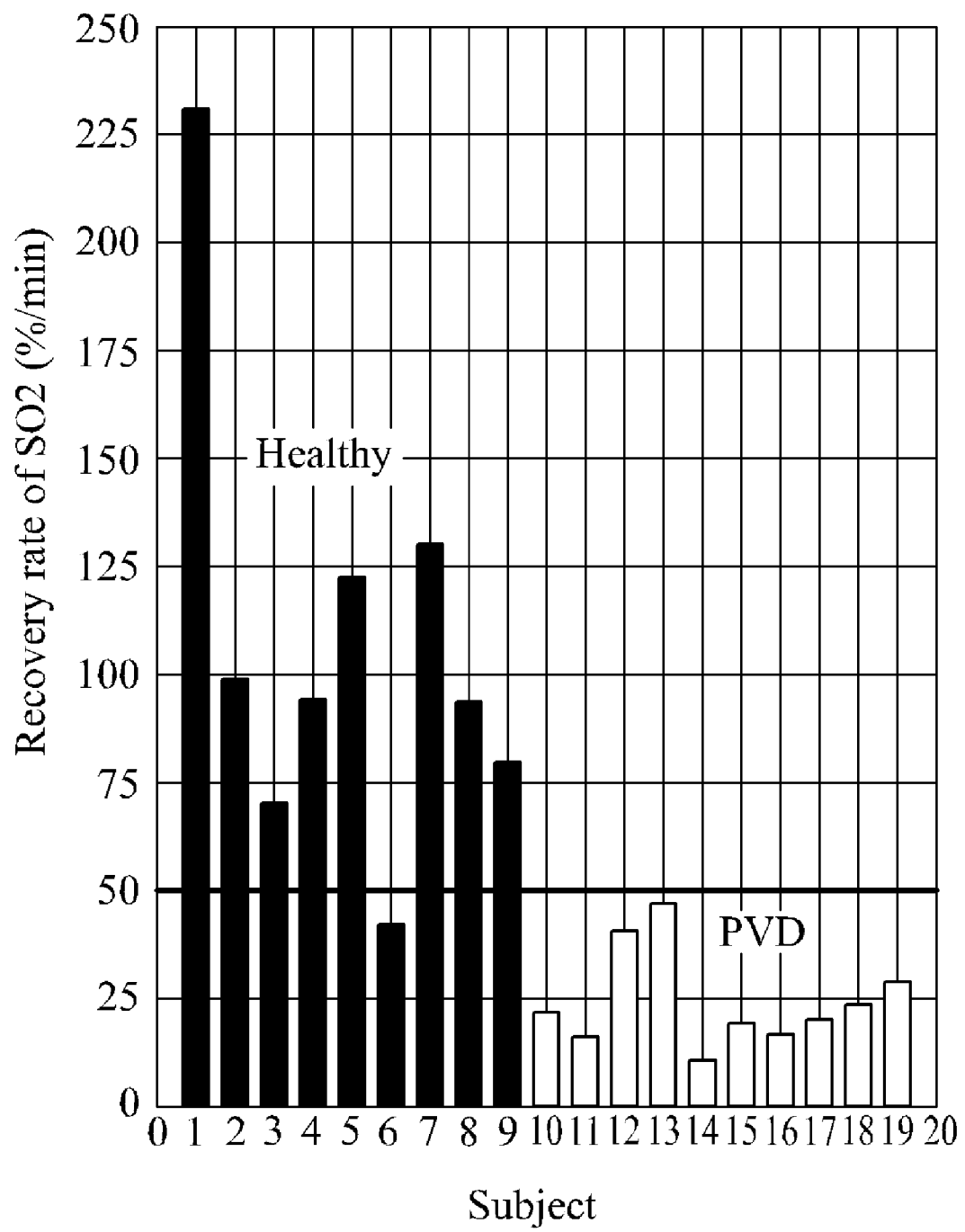
FIG. 6 shows a bar graph of various patients and diagnoses of peripheral vascular disease utilizing the rate of recovery of oxygen saturation.

FIG. 6 shows a bar graph of the rate of change of oxygen saturation during recovery for various patients. As shown, healthy patients have typically a higher rate of change of oxygen saturation during recovery. Accordingly a diagnosis of peripheral vascular disease can be made based on whether the rate of change oxygen saturation crosses a threshold (in this case is below a threshold), such as is shown in FIG. 6.

FIG. 7 shows results utilizing this technique for diagnosing peripheral vascular disease. As shown, there were ten true positives, eight true negatives, no false negatives and only one false positive.

Figure 8:
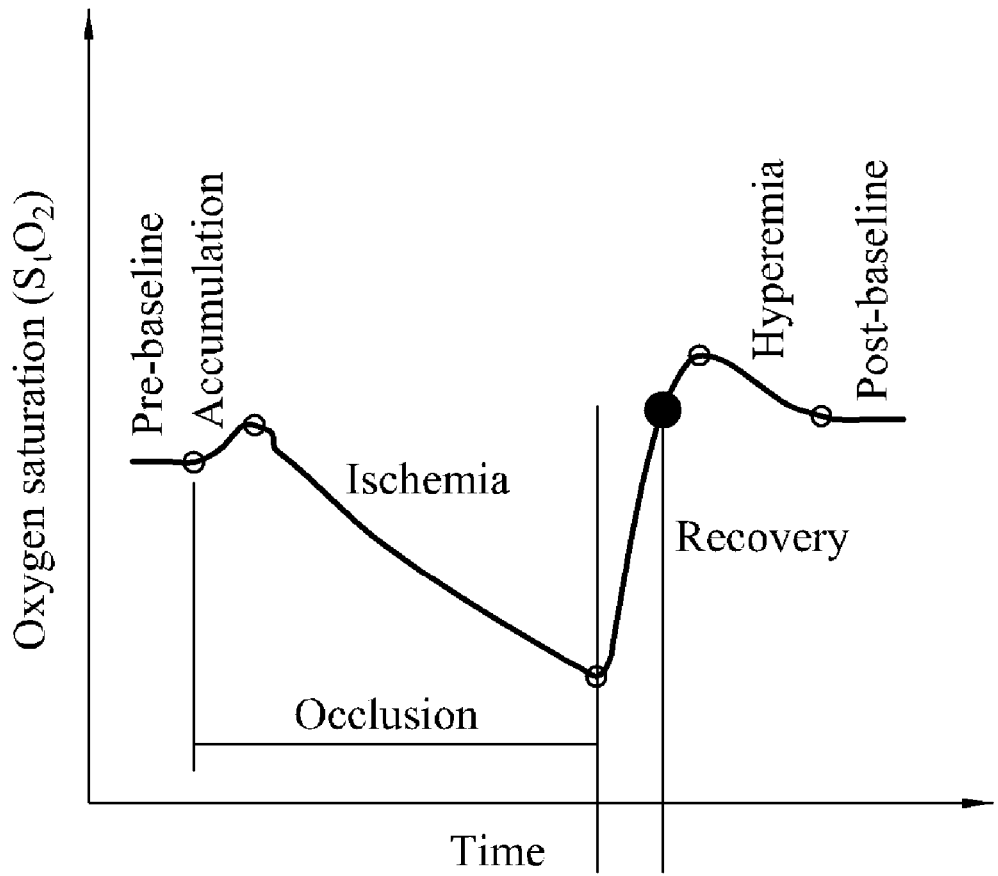
FIG. 8 shows a graph including the time for oxygen saturation to recover to a specified percentage during recovery from ischemia.

In another embodiment, the change in oxygen saturation during recovery is measured by the time for oxygen saturation to recover a specified percentage. FIG. 8 shows a graph of the time needed for oxygen saturation to recover 80 percent of the oxygen saturation through the recovery phase.

Figure 9:
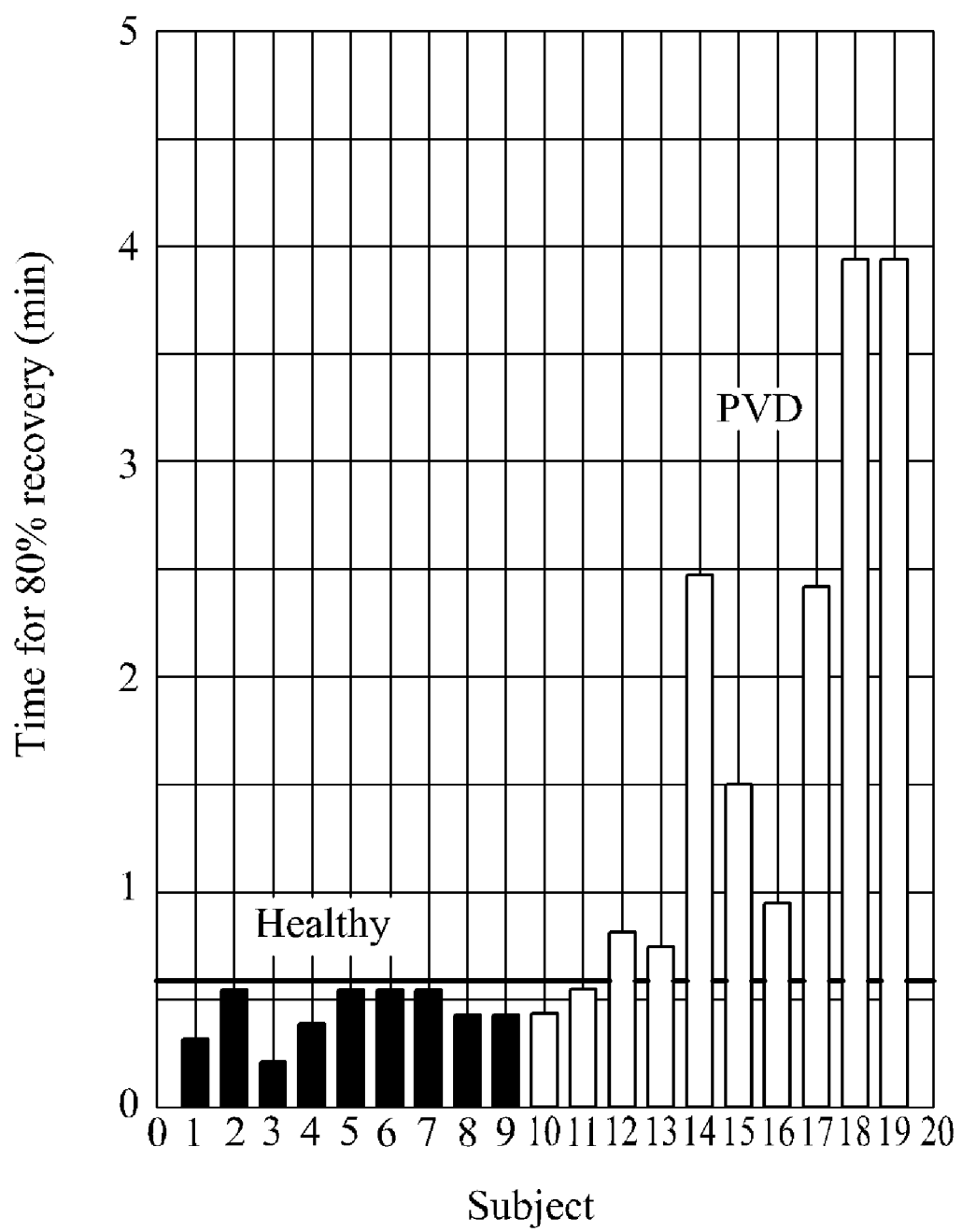
FIG. 9 shows a bar graph of various patients and the diagnoses of peripheral vascular disease utilizing the time for oxygen saturation to recover a specified percentage.

FIG. 9 shows a bar graph of the time for oxygen saturation to recover to a specified percentage during recovery for various individuals. As shown, patients with peripheral vascular disease demonstrated more time was taken to recover oxygen saturation to 80 percent. Accordingly, peripheral vascular disease can be diagnosed according to whether the time for oxygen saturation to recover a specified percentage crosses a threshold (in this case is above a threshold) as shown in FIG. 9.

Figure 10:
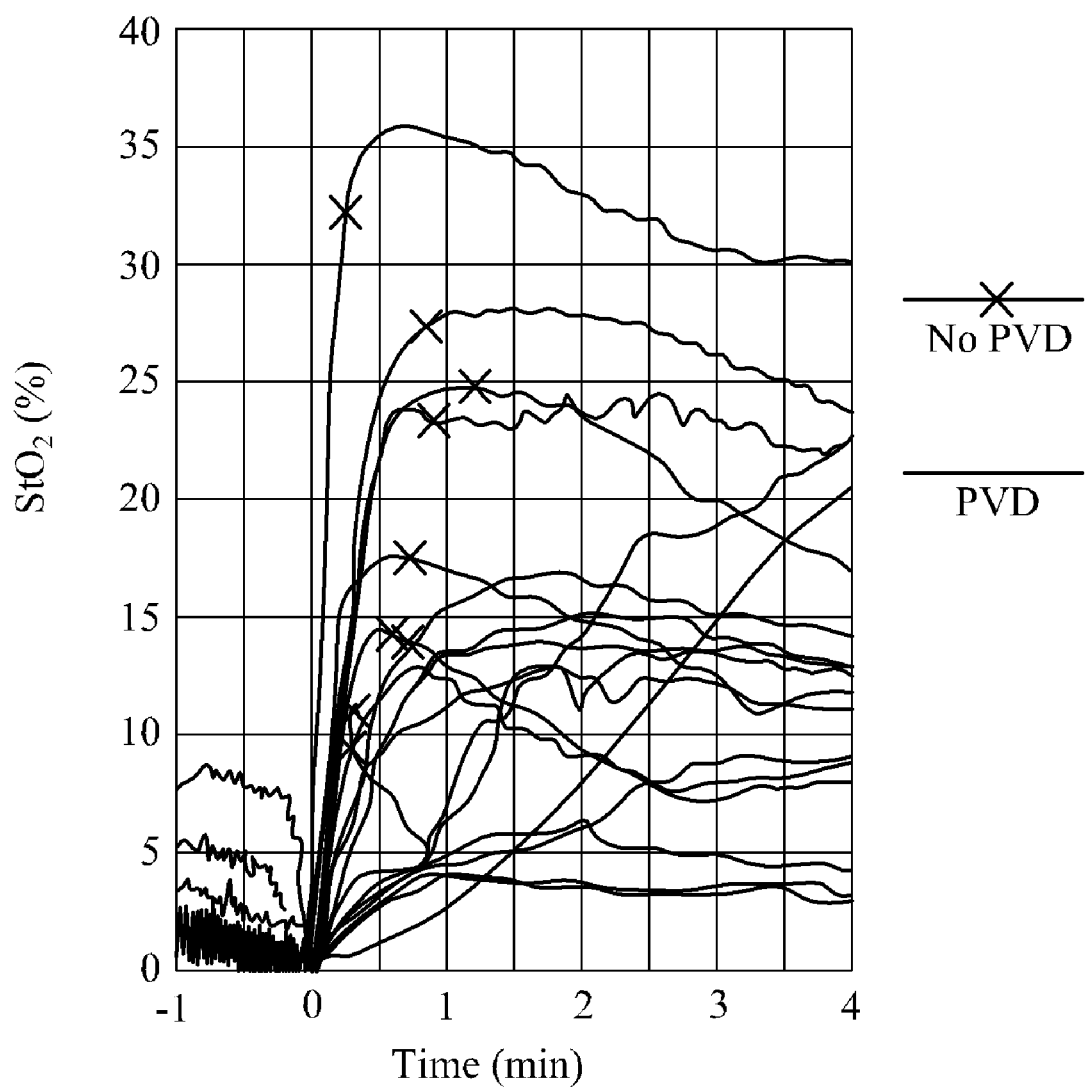
FIG. 10 shows a graph of patients and their oxygen saturation recovery over time.

FIG. 10 shows a graph of the oxygen saturation in tissue of patients over time for patients without peripheral vascular disease and with peripheral vascular disease. As shown, patients without peripheral vascular disease typically recover oxygen saturation more quickly than patients with peripheral vascular disease.

FIG. 11 shows results from varies patients utilizing this technique for diagnosing peripheral vascular disease. As shown, there were eight true positives, nine true negative, zero false positives and only two false negatives.

Although the preceding has described different methods for measuring changes in oxygen saturation during recovery, the invention can utilize any methods of measuring any changes oxygen saturation. Additionally, one or more different methods of measuring changes in oxygen saturation during recovery can be combined in order to provide diagnoses for peripheral vascular disease.

Figure 12:
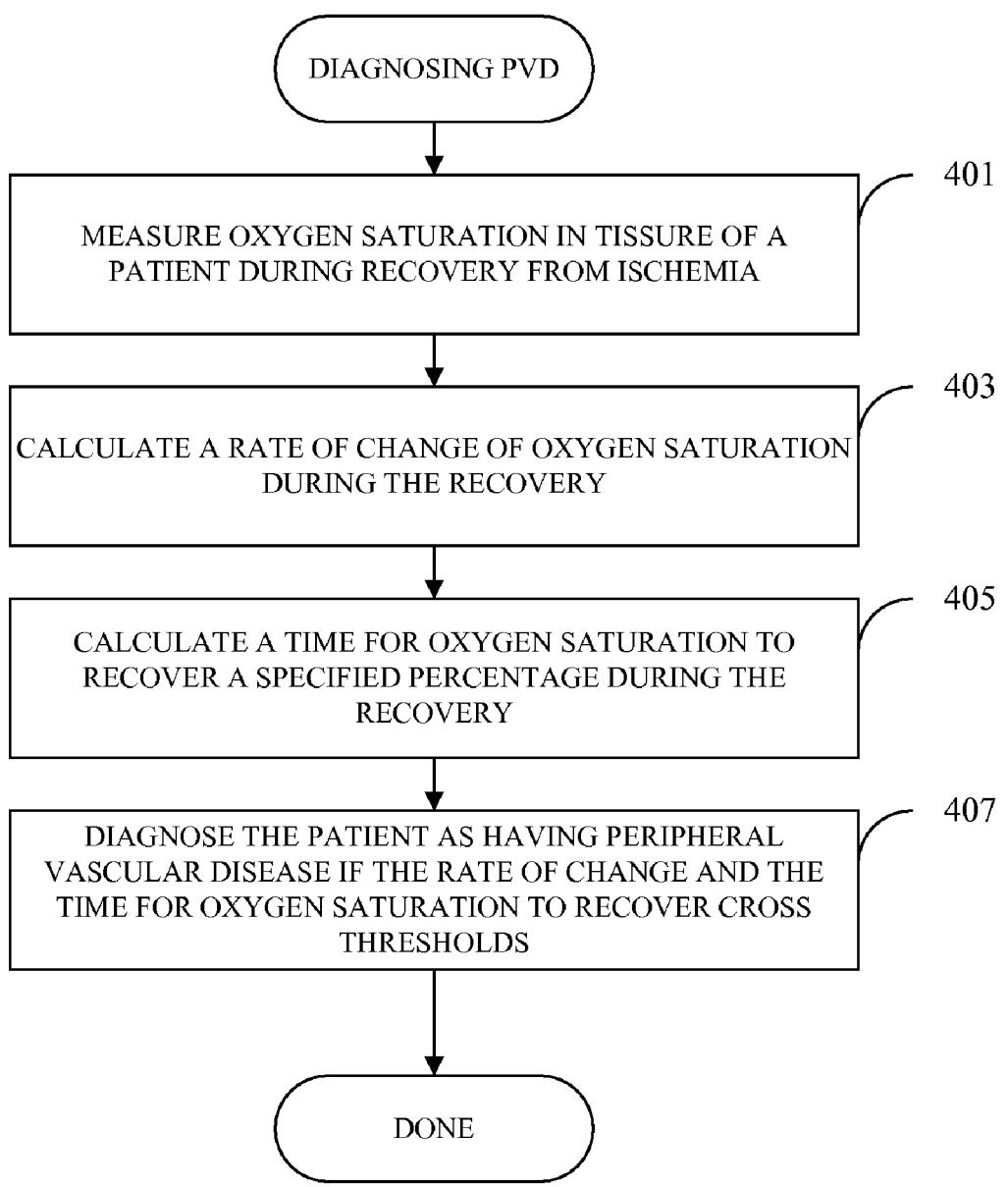
FIG. 12 shows a flow chart of another process of diagnosing peripheral vascular disease according to the invention.

FIG. 12 shows a flow chart of another process of diagnosing peripheral vascular disease. At a step 401, oxygen saturation in tissue of a patient during recovery from ischemia is measured. A rate of change of oxygen saturation during the recovery is calculated at a step 403. The rate of change can be calculated as described previously. At a step 405, a time for oxygen saturation to recover a specified percentage during the recovery is calculated. The time can be calculated as discussed previously.

At a step 407, the patient can be diagnosed as having peripheral vascular disease if the rate of change and the time for oxygen saturation to recover cross thresholds. By utilizing multiple methods of measuring changes in oxygen saturation during recovery, greater accuracy in diagnosing peripheral vascular disease can be obtained.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method of diagnosing peripheral vascular disease comprising:
   measuring oxygen saturation in tissue of a patient during an accumulation phase prior to ischemia;
   analyzing the oxygen saturation in the tissue during the accumulation phase; and
   diagnosing the patient as having peripheral vascular disease according to changes in the oxygen saturation in the tissue during the accumulation phase.

2. The method of claim 1 wherein the analyzing the oxygen saturation comprises calculating a rate of change of oxygen saturation during the accumulation phase.

3. The method of claim 2 wherein the rate of change is calculated at a midpoint of the accumulation phase.

4. The method of claim 2 wherein the diagnosing the patient comprises determining if the rate of change crosses a threshold.

5. The method of claim 1 wherein the analyzing the oxygen saturation comprises calculating a time for oxygen saturation to reach a specified percentage during the accumulation phase.

6. The method of claim 5 wherein the diagnosing the patient comprises determining if the time for oxygen saturation to reach a specified percentage crosses a threshold.

7. The method of claim 1 wherein the analyzing the oxygen saturation comprises:
   calculating a rate of change of oxygen saturation during the accumulation phase; and
   calculating a time for oxygen saturation to reach a specified percentage during the accumulation phase.

8. The method of claim 7 wherein the diagnosing the patient comprises determining if the rate of change and the time for oxygen saturation during the accumulation phase cross thresholds.

9. A method comprising:
   measuring oxygen saturation of the tissue of the patient during an accumulation phase prior to ischemia; and
   diagnosing the patient as having peripheral vascular disease based on changes in the oxygen saturation of the tissue during an accumulation phase before ischemia.

10. The method of claim 9 comprising:
    providing a visual indication of a positive diagnosis of peripheral vascular disease on a display when a measured rate of change in the oxygen saturation during an accumulation phase crosses a threshold value.

11. The method of claim 9 comprising
    providing a visual indication of a positive diagnosis of peripheral vascular disease on a display when a measured time for the oxygen saturation to cross a percentage value during the accumulation phase exceeds a specific time value.

12. The method of claim 9 comprising:
    providing a visual indication of a positive diagnosis of peripheral vascular disease on a display when a measured time, from a starting time value to an ending time value, for the oxygen saturation to cross a percentage value exceeds a specific time value, wherein the ending time is within the accumulation phase.

13. The method of claim 9 comprising:
    providing a visual indication of a positive diagnosis of peripheral vascular disease on a display when a measured time, from a starting time value to an ending time value, for the oxygen saturation to cross a percentage value exceeds a specific time value, wherein the starting time is within the accumulation phase.

14. A system for diagnosing peripheral vascular disease comprising:
    a probe comprising a first detector input;
    a computer, coupled to process signals received via the first detector input, to determine changes in oxygen saturation in tissue of a patient and make a diagnosis of peripheral vascular disease based on the oxygen saturation changes during an accumulation phase;
    a pressure cuff, attachable to the patient, to cause the accumulation phase in the patient; and
    a display, coupled to the computer, to provide a visual indication of a positive diagnosis of peripheral vascular disease.

15. The system of claim 14 wherein the probe comprises a second detector input and a source output, and a first distance between the first detector input and the source output is different from a second distance between the second detector input and the source output.

16. The system of claim 14 wherein the probe comprises a second detector input, a first source output, and a second source output, and a first distance between the first detector input and the first source output is different from a second distance between the second detector input and the second source output.

17. The system of claim 14 wherein the probe comprises a second detector input, a first source output, and a second source output, and a first distance between the first detector input and the first source output is substantially the same as a second distance between the second detector input and the second source output.

18. A system for diagnosing peripheral vascular disease comprising:
- a probe comprising a first detector input;
- a computer, coupled to process signals received via the first detector input, to determine changes in oxygen saturation in tissue of a patient and make a diagnosis of peripheral vascular disease based on the oxygen saturation changes during an accumulation phase; and
- a display, coupled to the computer, to provide a visual indication of a positive diagnosis of peripheral vascular disease,
- wherein the diagnosis of peripheral vascular disease is positive when the computer determines a rate of change in the oxygen saturation crosses a threshold value during the accumulation phase before ischemia.

19. A system for diagnosing peripheral vascular disease comprising:
- a probe comprising a first detector input;
- a computer, coupled to process signals received via the first detector input, to determine changes in oxygen saturation in tissue of a patient and make a diagnosis of peripheral vascular disease based on the oxygen saturation changes during an accumulation phase; and
- a display, coupled to the computer, to provide a visual indication of a positive diagnosis of peripheral vascular disease,
- wherein the diagnosis of peripheral vascular disease is positive when a measured time for the oxygen saturation to cross a percentage value during the accumulation phase before ischemia exceeds a specific time value.

20. A system for diagnosing peripheral vascular disease comprising:
- a probe comprising a first detector input;
- a computer, coupled to process signals received via the first detector input, to determine changes in oxygen saturation in tissue of a patient and make a diagnosis of peripheral vascular disease based on the oxygen saturation changes during an accumulation phase; and
- a display, coupled to the computer, to provide a visual indication of a positive diagnosis of peripheral vascular disease,
- wherein the diagnosis of peripheral vascular disease is positive when a measured time, from a starting time value to an ending time value, for the oxygen saturation to cross a percentage value exceeds a specific time value, and the ending time is within the accumulation phase before ischemia.

21. A system for diagnosing peripheral vascular disease comprising:
- a probe comprising a first detector input;
- a computer, coupled to process signals received via the first detector input, to determine changes in oxygen saturation in tissue of a patient and make a diagnosis of peripheral vascular disease based on the oxygen saturation changes during an accumulation phase; and
- a display, coupled to the computer, to provide a visual indication of a positive diagnosis of peripheral vascular disease,
- wherein the diagnosis of peripheral vascular disease is positive when a measured time, from a starting time value to an ending time value, for the oxygen saturation to cross a percentage value exceeds a specific time value, and the starting time is within the accumulation phase before ischemia.

* * * * *